(12) United States Patent
Johnson

(10) Patent No.: US 7,663,015 B2
(45) Date of Patent: Feb. 16, 2010

(54) TRAUMATIC AMPUTATION AND WOUND DRESSING

(75) Inventor: Ross A. Johnson, Anderson, SC (US)

(73) Assignee: Tactical Medical Solutions, Inc., Anderson, SC (US)

( * ) Notice: Subject to any disclaimer, the term of this patent is extended or adjusted under 35 U.S.C. 154(b) by 0 days.

(21) Appl. No.: 11/838,159

(22) Filed: Aug. 13, 2007

(65) Prior Publication Data

US 2008/0039762 A1 Feb. 14, 2008

Related U.S. Application Data

(60) Provisional application No. 60/822,221, filed on Aug. 11, 2006.

(51) Int. Cl.
*A61F 13/00* (2006.01)
(52) U.S. Cl. .................................... 602/42; 128/888
(58) Field of Classification Search ............. 602/41–45; 128/888–889
See application file for complete search history.

(56) References Cited

U.S. PATENT DOCUMENTS

| | | | |
|---|---|---|---|
| 3,491,753 A | 1/1970 | Milton et al. | |
| 4,085,746 A | 4/1978 | Castiglia | |
| 4,926,848 A * | 5/1990 | Shimkus et al. | 602/75 |
| 5,107,827 A | 4/1992 | Boyd | |
| 5,480,377 A | 1/1996 | Cartmell et al. | |
| 5,538,500 A | 7/1996 | Peterson | |
| 5,722,943 A | 3/1998 | Sessions | |
| 5,891,078 A | 4/1999 | Turngren et al. | |
| 6,545,193 B1 * | 4/2003 | Morgenstern | 602/41 |
| 6,573,419 B2 * | 6/2003 | Naimer | 602/41 |
| 2002/0128579 A1 | 9/2002 | Church | |
| 2003/0149389 A1 * | 8/2003 | Daneshvar | 602/52 |
| 2005/0256439 A1 | 11/2005 | Grossman | |
| 2006/0163101 A1 | 7/2006 | Assie et al. | |

* cited by examiner

Primary Examiner—Michael A. Brown
(74) Attorney, Agent, or Firm—Cahn & Samuels LLP

(57) ABSTRACT

An integrated and complete dressing for the care and treatment of traumatic amputations and wounds. The traumatic amputation and wound dressing includes an oversized wound pad, an elastic bandage, and fasteners in an integrated unit for quickly and effectively treating an amputation. The elastic bandage may be attached to the wound pad such that the bandage forms an angle of about 90 degrees with respect to a vertical axis of the wound pad. The wound pad can be readily folded over an amputation and quickly wrapped with the elastic bandage. The fasteners may be attached to the periphery of the wound pad. When the dressing is applied to a stump of an amputated limb and the fasteners are engaged, the wound pad is relatively securely held in position and downward pressure is exerted on the stump. In some embodiments, the elastic bandage may also include brakes designed to prevent the bandage from unintentionally unraveling. The brakes also facilitate application of the dressing to the stump.

4 Claims, 3 Drawing Sheets

TRAUMATIC AMPUTATION AND WOUND DRESSING

I. CROSS REFERENCE TO RELATED APPLICATION

This application claims the benefit of U.S. Provisional Patent Application No. 60/822,221, filed Aug. 11, 2006, which is incorporated herein by reference.

II. FIELD OF THE INVENTION

The present invention relates to a dressing for the care and treatment of traumatic amputations, large pattern wounds and burns. More particularly, the present invention relates to a traumatic amputation and wound dressing and method of applying the dressing for quickly and effectively treating an amputation, large pattern wound or burn.

III. BACKGROUND OF THE INVENTION

Traumatic amputations are generally gruesome, devastating injuries that may result in death. These injuries frequently result in extreme blood loss which can contribute greatly to the associated fatality rate. The time required to control the bleeding of an amputation is vital in reducing blood loss. Because these injuries often occur in dire conditions, such as severe accidents or on the battlefield, where medical attention is not always readily available, it is critically important that the victims (who often have to treat themselves) or caregivers (medics, first responders, or medical providers) quickly control and stop the bleeding.

The most commonly used treatment to control bleeding arising from amputations, large wounds, and burns is the elastic bandage, often along with another treatment material, such as gauze or a wound pad. These bandages are well-known in the prior art and have been used for many years. Caregivers often simply wrap amputation stumps with an elastic bandage attempting to apply great pressure to the wound in hopes that the pressure will help control the bleeding. Still, it is often not possible to apply sufficient pressure to the stump to control the bleeding as it is difficult to control or stop the bleeding relying on pressure alone. As such, caregivers also have been found to use some type of treatment material, such as gauze or an absorbent pad, to cover the wound prior to applying the elastic bandage over the dressing. The treatment material helps to apply pressure to the wound and aids in controlling bleeding. However, the material often comes undone during handling—which frequently requires multiple separate packaging components, i.e. gauze, wound pad, elastic bandage and/or tape or other fasteners.

In addition to controlling bleeding, these treatment materials provide an important function of covering and protecting open wounds. Quickly covering the wounds helps to prevent the risk of contamination and the infection that contamination causes. However, these materials are often cumbersome to handle and difficult to appropriately apply, particularly on an immobilized victim. These difficulties are further complicated by the multiple components necessary to properly wrap and package a stump.

It is therefore important that the material used to cover and wrap stumps resulting from amputations be easy to use so as to not be unnecessarily handled—causing further contamination. It is also important that these materials are able to be quickly and easily applied to the amputation.

Notwithstanding the usefulness of the above-described methods, a need still exists for traumatic amputation dressing, particularly an amputation dressing that quickly covers and wraps an amputation so as to both expeditiously control bleeding and prevent further contamination.

IV. SUMMARY OF THE INVENTION

In accordance with an embodiment of the invention, a traumatic wound dressing is provided. The dressing includes an oversized wound pad; an elastic bandage attached to a peripheral point of said oversized wound pad; and at least one brake disposed on said elastic bandage to maintain said bandage in a rolled condition. The oversized wound pad is of sufficient size to envelope an amputated limb of an average sized human and the elastic bandage is of sufficient length to wrap several times around a stump of an amputated limb and the oversized wound pad. The dressing may also include a pouch on the elastic bandage and/or wound pad that contains at least one treatment material. The dressing may further include at least one fastener attached to at least one side of the wound pad.

In accordance with another embodiment of the invention, a process of applying a dressing to an amputation is provided. The process includes contacting a severed limb with an oversized wound pad, wherein said wound pad is of sufficient size to envelope said severed limb; folding said wound pad over said severed limb to substantially envelope said limb; and wrapping an elastic bandage that is attached at a right angle to a corner of said wound pad around said severed limb and said folded wound pad.

In accordance with a further embodiment of the invention, a traumatic amputation dressing is provided. The dressing includes means for enveloping a severed limb; means for securing said enveloping means to said severed limb; and means for storing treatment material. The means for enveloping a severed limb and/or the means for securing may include means for storing treatment material for treating the severed limb.

V. BRIEF DESCRIPTION OF THE DRAWINGS

The present invention is described with reference to the accompanying drawings, wherein.

Given the following enabling description of the drawings, the apparatus should become evident to a person of ordinary skill in the art.

VI. DETAILED DESCRIPTION OF THE DRAWINGS

Figure 1:
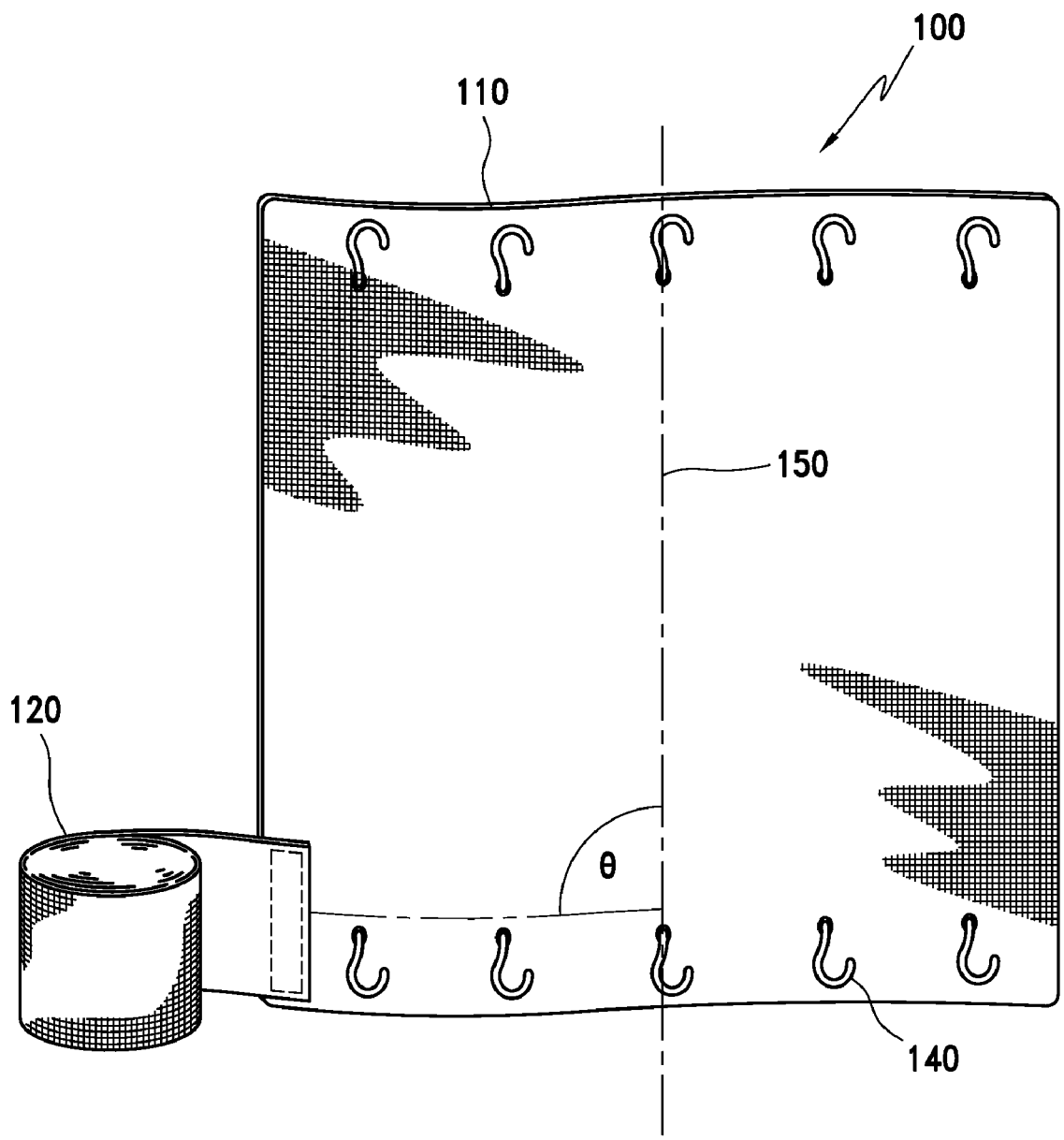
FIG. 1 illustrates a traumatic amputation and wound dressing according to an exemplary embodiment of the present invention.

The present invention as illustrated, for example, in FIG. 1 is directed to a traumatic amputation dressing 100 for application on a stump of a severed or amputated limb of a human. The dressing 100 may also be used to cover burns or large pattern wound, such as shrapnel wounds. The dressing 100 includes at least one oversized wound pad 110 and an elastic bandage 120. The wound pad 110 is preferably of sufficient size to envelope the stump of a severed limb, or to cover the entire back or chest of an average sized human. Suitable wound pads have areas of about 16 inches by 24 inches, 20 inches by 20 inches, or the like. The elastic bandage 120 is attached to a corner of the wound pad 110. The elastic bandage is preferably at least 3" to 6" in width and several feet in length. Because the elastic bandage 120 is attached to the wound pad 110 the resulting integrated traumatic amputation dressing 100 is more readily applied to the amputation, large pattern wound, or burn.

In accordance with the present invention, as illustrated in FIG. 1, the elastic bandage 120 may be attached to a peripheral point, e.g., a corner of wound pad 110. The elastic bandage 120 may be attached to the wound pad 110 such that an angle θ of about 90 degrees is formed with respect to a vertical axis 150 of the wound pad 110. In some embodiments, the wound pad 110 also includes fasteners 140 situated along one or more sides, preferably two opposing sides, of the wound pad 110. The wound pad 110 may be constructed of gauze or other known materials, including translucent or transparent plastic materials, such as PETG, that allow individuals to see through the wound pad and therefore determine if bleeding has been stopped. The fasteners 140, which may comprise hooks, Velcro®, adhesive or the like, are designed to affix to each other and envelope the stump of the amputated limb with the wound pad 110. The fasteners 140 fix the wound pad 110 in place on the stump and also generate a downward pressure on the stump. Properly positioning the wound pad 110 and applying a downward pressure on the stump both assist in controlling bleeding. However, the dressing functions efficiently whether or not such alignment is achieved.

The dressing 100 is packaged with the wound pad 110 folded and the elastic bandage 120 rolled. In use, the wound pad 110 is unfolded and the center of the wound pad 110 is applied directly to the end of the stump. It may be desirable to align the center of wound pad 110 with the stump. Once aligned, the wound pad 110 is folded over the stump so as to form an envelope around the stump. The optional opposing fasteners 140, when included, are then affixed to each other thereby holding the wound pad 110 in place and providing downward pressure to the stump. The ends of the wound pad 110 may then be folded down around the ends of the stump and the elastic bandage 120 wrapped around the folded wound pad 110.

The elastic bandage 120 may also include spaced "brakes" disposed along the length of the bandage. The brakes may comprise Velcro®, an adhesive or the like and act to prevent the unintentional unraveling of the elastic bandage. The brakes may also act to help more effectively exert pressure on the stump by maintaining tension on the bandage during wrapping. The brakes also provide a more secure final packaging of the dressing on the amputation. An exemplary elastic bandage provided with brakes is described in U.S. patent application Ser. No. 11/745,184 which is herein incorporated by reference.

Figure 2:
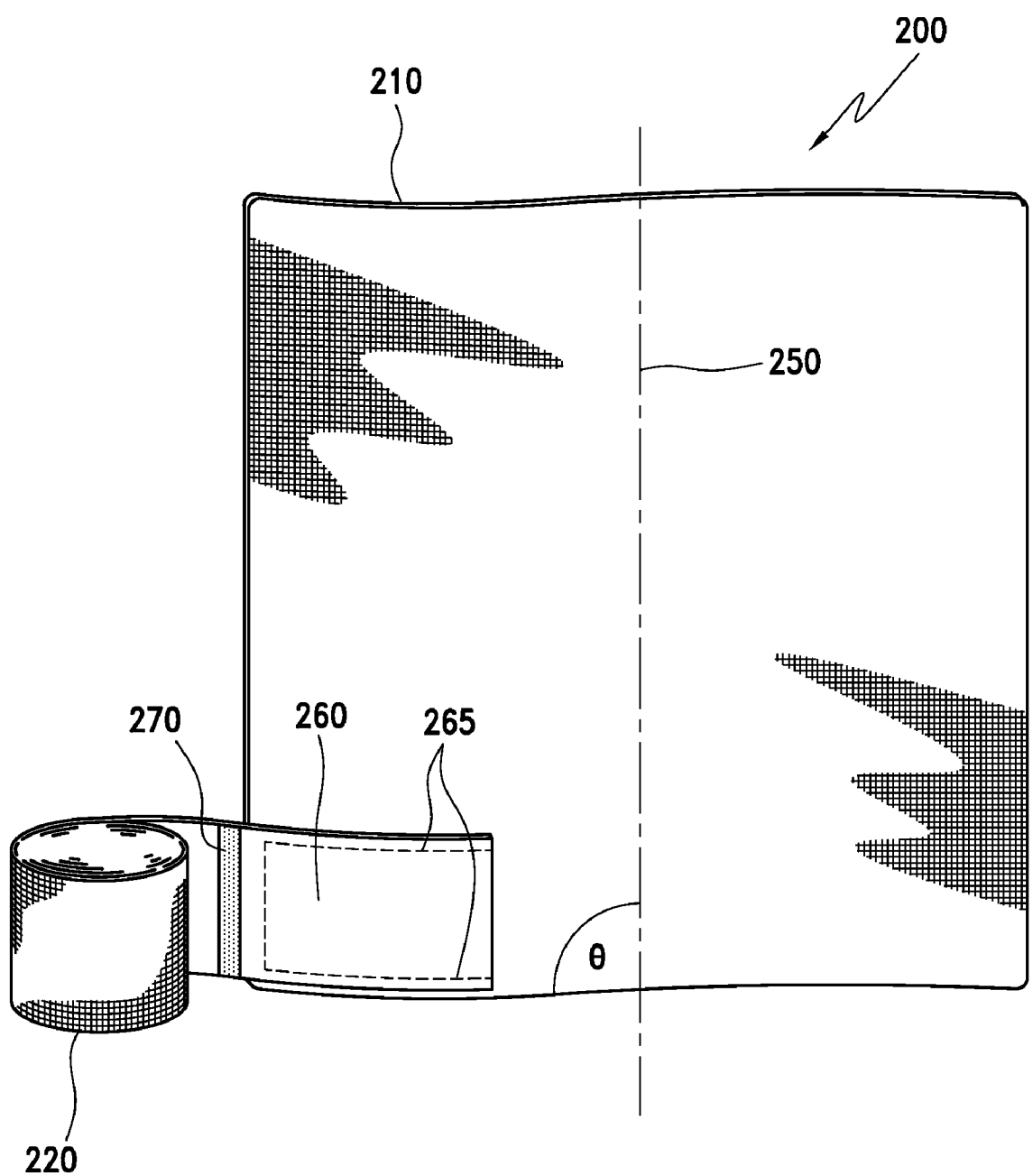
FIG. 2 illustrates an alternative traumatic amputation and wound dressing according to exemplary embodiment of the present invention.

In accordance with an alternative embodiment of the present invention, as illustrated in FIG. 2, an elastic bandage 220 may be attached to a corner of a wound pad 210 to form substantially a 90 degree angle θ with a vertical axis 250 of the wound pad 210. The elastic bandage 220 may include a receptacle 260 formed on the bandage 220. The receptacle 260 may be formed by creating a pocket between two opposing pieces of material of the bandage 220, for example by placing stitches 265 along the perimeter of opposing pieces of material of the bandage 220. The receptacle 260 may contain an additional wound treatment material. The wound treatment material may include, for example, gauze for assistance with controlling bleeding and/or plastic sheeting for creating an occlusion layer over the wound. The treatment material may be applied to the wound prior to wrapping with the wound pad 210 or bandage 220, such that bleeding is better controlled and stabilization of the wound is promoted. The bandage 220 may also include one or more fasteners 270, such as Velcro®, an adhesive, or the like to further assist wrapping and packaging of the wound.

Figure 3:
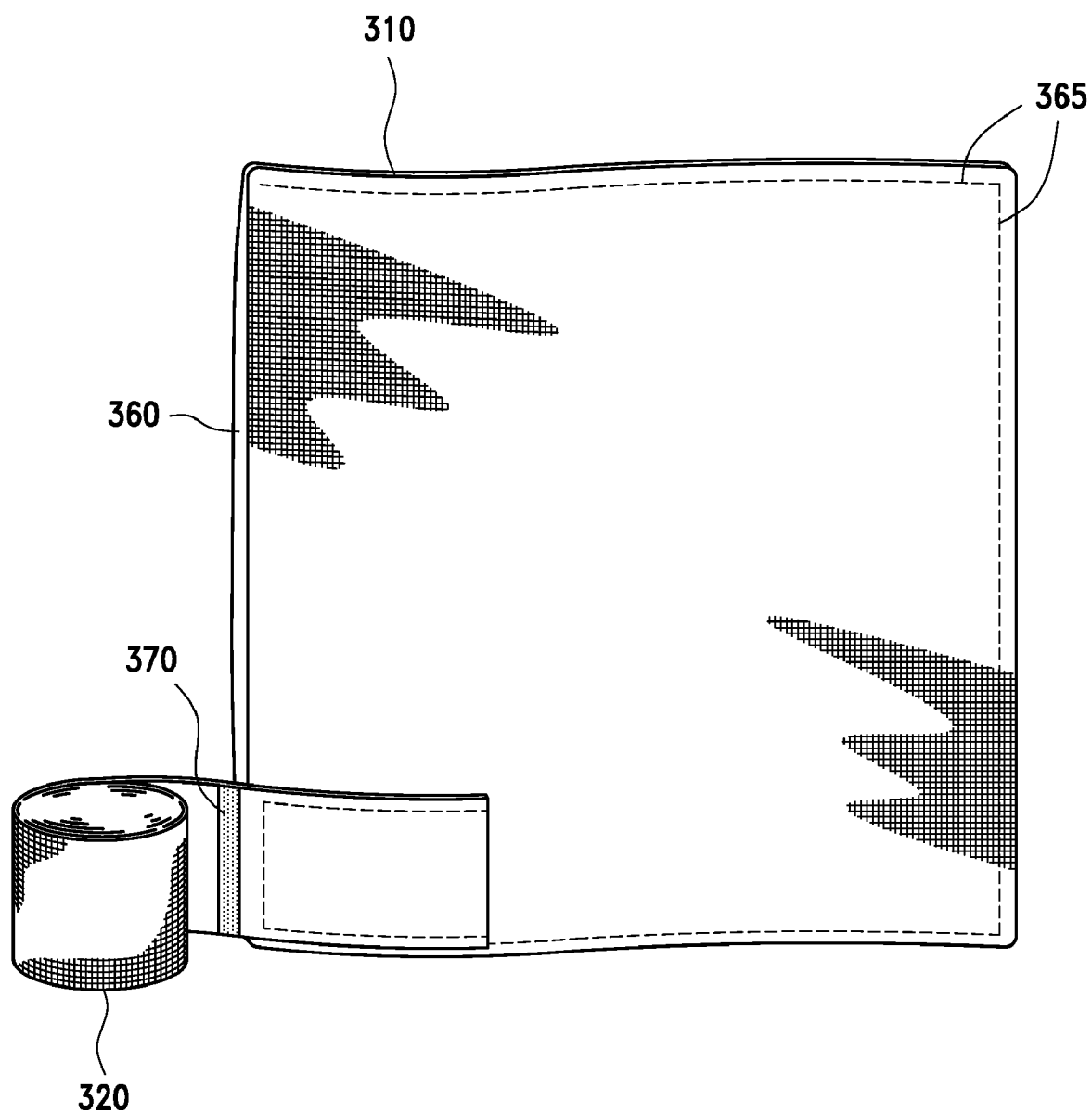
FIG. 3 illustrates another alternative traumatic amputation and wound dressing according to an exemplary embodiment of the invention.

In accordance with another alternative embodiment of the present invention, as illustrated in FIG. 3, an elastic bandage 320 may be attached to a corner of the wound pad 310. However, this embodiment includes a receptacle 360 within the wound pad. The receptacle 360 may be formed by creating a pocket in opposing pieces of material of the wound pad 310, for example by placing stitches 365 in the opposing pieces of material along one or more sides. Treatment material, such as gauze or occlusive plastic, may be stored in the receptacle and applied to the wound prior to wrapping with the wound pad 310 or bandage 320. The treatment material along with the wound pad acts to better control and stabilize the wound. The bandage 320 may also include one or more fasteners 370, such as Velcro®, an adhesive, or the like to further assist wrapping and packaging of the wound.

Although the present invention has been described in terms of particular preferred and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the preferred and alternative embodiments described above can be configured without departing from the scope and spirit of the invention. Therefore, it is to be understood that, within the scope of the appended claims, the invention may be practiced other than as specifically described herein.

VII. INDUSTRIAL APPLICABILITY

The above-described invention is useful for the quick and easy dressing of amputations. The invention provides an integrated and complete solution for reducing the time required and complications associated with dressing an amputation. The invention is particularly useful in providing means for quickly controlling bleeding in situations where there are limited treatment materials or where time is vital.

I claim:

1. A process of applying a dressing to a severed limb, comprising:
    Contacting a stump of the severed limb with an oversized wound pad, wherein said wound pad is of sufficient size to envelope said severed limb;
    folding said wound pad over said severed limb to substantially envelope said limb; and
    wrapping an elastic bandage that is attached at a right angle to a corner of said wound pad around said severed limb and said folded wound pad.

2. The traumatic wound dressing according to claim 1 further comprising:
    prior to contacting the severed limb with an oversized wound pad, performing the following:
    removing treatment material stored in a pouch on said bandage or said wound pad; and
    applying said treatment material to said severed limb.

3. The process according to claim 1, further comprising:
    prior to wrapping said elastic bandage around said severed limb and said folded wound pad, performing the following:
    engaging at least one fastener affixed to at least one side of said wound pad such that the wound pad is held in place and pressure is applied to the stump of the severed limb.

4. The process of claim 1 further comprising aligning a center of the wound pad with the stump.

* * * * *